United States Patent
Burckhardt et al.

(10) Patent No.: US 10,662,280 B2
(45) Date of Patent: May 26, 2020

(54) AMINE FOR LOW-EMISSION EPOXY RESIN COMPOSITIONS

(71) Applicant: SIKA TECHNOLOGY AG, Baar (CH)

(72) Inventors: Urs Burckhardt, Zürich (CH); Ursula Stadelmann, Zürich (CH); Andreas Kramer, Zürich (CH); Edis Kasemi, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/746,529

(22) PCT Filed: Aug. 4, 2016

(86) PCT No.: PCT/EP2016/068704
§ 371 (c)(1),
(2) Date: Jan. 22, 2018

(87) PCT Pub. No.: WO2017/025448
PCT Pub. Date: Feb. 16, 2017

(65) Prior Publication Data
US 2018/0215863 A1    Aug. 2, 2018

(30) Foreign Application Priority Data

Aug. 7, 2015 (EP) .................................. 15180243

(51) Int. Cl.
*C08G 59/50* (2006.01)
*C08G 59/56* (2006.01)
*C07C 217/34* (2006.01)
*C07C 217/32* (2006.01)
*C09D 163/00* (2006.01)

(52) U.S. Cl.
CPC .......... *C08G 59/504* (2013.01); *C07C 217/32* (2013.01); *C07C 217/34* (2013.01); *C08G 59/50* (2013.01); *C08G 59/56* (2013.01); *C09D 163/00* (2013.01)

(58) Field of Classification Search
CPC ...... C08G 59/504; C08G 59/50; C08G 59/56; C07C 217/32; C07C 217/34; C09D 163/00
USPC ........................................................ 523/400
See application file for complete search history.

(56) References Cited

U.S. PATENT DOCUMENTS 6,165,558 A * 12/2000 Schneider ............ C08G 59/184
427/386

FOREIGN PATENT DOCUMENTS

| CA | 877389 A | 8/1971 |
|---|---|---|
| CN | 1093146 C | 10/2002 |
| DE | 1912485 A1 | 11/1969 |
| WO | 97/028203 A1 | 8/1997 |

OTHER PUBLICATIONS

Sep. 15, 2016 International Search Report issued in International Patent Application No. PCT/EP2016/068704.
Feb. 13, 2018 International Preliminary Report on Patentability issued in International Patent Application No. PCT/EP2016/068704.
Oct. 11, 2019 Office Action issued in Chinese Patent Application No. 201680046320.8.

* cited by examiner

*Primary Examiner* — David T Karst
(74) *Attorney, Agent, or Firm* — Oliff PLC

(57) ABSTRACT

An amine of formula (I) in a curing agent for epoxy resins, a curing agent for epoxy resins containing the amine of formula (I) and resultant epoxy resin compositions which can be used particularly as low-emission room-temperature-curing epoxy resin coatings demonstrating good workability, rapid curing, a high degree of hardness and high surface quality. The amine of formula (I) is low-odour, can be handled well at room temperature even without dilution, and can be produced at high purity in a simple process.

15 Claims, No Drawings

AMINE FOR LOW-EMISSION EPOXY RESIN COMPOSITIONS

TECHNICAL FIELD

The invention pertains to the field of amines, hardeners for epoxy resins, epoxy resin compositions, and their use, particularly as coating, covering or paint.

PRIOR ART

Epoxy resin compositions that are suitable for coating purposes are to have an extremely low viscosity so that they can be processed effectively at ambient temperature. They are also to cure very rapidly and without disruption, even under humid and cold conditions, while forming an even surface without hazing, speckling or craters. Lastly, a fully cured coating is to possess high hardness with low brittleness, in order to withstand mechanical stressing as effectively as possible. For optically demanding applications, such as top coverings on floors, for example, a coating, moreover, is to exhibit high gloss and as little as possible a tendency toward yellowing under the effect of light. Hardeners known from the prior art for epoxy resin coatings typically comprise reaction products ("adducts") from the reaction of polyamines with epoxides, in particular with liquid bisphenol resins. Such adducts enable rapid curing but are of very high viscosity, which is why the hardeners, in order to set a manageable viscosity, customarily include considerable fractions of unadducted, low molecular mass polyamines and/or diluents. The unadducted polyamines typically have an intense odor, and they lead to increased incidence of blushing effects. "Blushing effects" are surface deficiencies which appear in the course of curing, such as hazing, speckles, roughness, and stickiness, and are caused by formation of salts ("blushing") between amines and carbon dioxide ($CO_2$) from the air, and occur particularly at high atmospheric humidity and low temperatures. The diluents typically lessen the blushing effects and enhance surface quality and coating brittleness, but are not incorporated into the resin matrix on curing and may be released by processes of evaporation or diffusion. Nowadays, however, the desire is increasingly for low-emission products which have a low content of releasable substances after curing. For low-emission epoxy resin compositions, therefore, diluents, such as benzyl alcohol, for example, can be used only in small quantities or not at all.

The high viscosity and susceptibility to blushing of the known adducts of polyamines with epoxides can be lowered not only by means of diluents but also by using the polyamine in a large excess at the adducting stage, and subsequently removing the unadducted excess by a separation technique. The removal of the polyamines typically used for adducting, such as IPDA, MXDA, DETA or TETA, however, is technically complex and usually incomplete, and the resulting reaction products mostly are still of high viscosity and/or are susceptible to blushing, and so it is hardly possible to do without diluents.

Coatings known as aqueous epoxy resin coatings are known from the prior art. They typically consist of an aqueous or water-thinnable hardener, typically comprising emulsified adducts of polyamines with epoxides, and of an aqueous epoxy resin emulsion. Aqueous and/or water-thinnable hardeners typically have water contents in the range from 10 to 80 weight %. Aqueous epoxy resin products are usually of low viscosity and low odor, but have other disadvantages. They are more expensive and substantially more complicated to prepare than nonaqueous products, can be applied only at sufficiently high temperature and in a relatively thin layer per operation, and exhibit increased sensitivity to water during and after curing.

SUMMARY OF THE INVENTION

It is an object of the present invention, therefore, to provide a low-viscosity and low-odor amine for use in hardeners for room-temperature-curing epoxy resin compositions, which allows access to low-emission epoxy resin compositions that have good processing qualities and rapid curing, resulting in coatings of high hardness and good surface quality.

This object is achieved with the amine of the formula (I) as described in claim 1. The viscosity of the amine of the formula (I) is low enough, surprisingly, that it can be readily managed at room temperature even without dilution. The amine of the formula (I), surprisingly, has hardly any tendency toward blushing effects. It can be prepared in high purity in a simple operation, and reaction products from this operation are low in odor, highly fluid at room temperature, contain little unreacted diamine, and do not have secondary products of relatively high molecular mass that correspond to the formula (I). In comparison to similar adducts known from the prior art and based on IPDA, MXDA, DETA or TETA, the amine of the formula (I) is more easily preparable in high purity, has a lower viscosity, and causes significantly fewer blushing effects.

The amine of the formula (I) affords low-emission epoxy resin compositions which are readily workable, cure rapidly, form high-quality plastics of high hardness and even, non-tacky surface with high gloss and, surprisingly, hardly yellow under the effect of light.

Further aspects of the invention are subjects of the further independent claims. Particularly preferred embodiments of the invention are subjects of the dependent claims.

EMBODIMENTS OF THE INVENTION

A subject of the invention is the use of an amine of formula (I) in a hardener for epoxy resins,

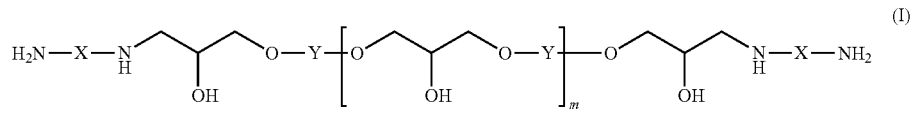

(I)

where
m is 0 to 3,
X is 1,2-ethylene or 1,2-propylene, and
Y is a monocyclic or polycyclic aromatic hydrocarbon radical.

Substance names beginning with "poly", such as polyamine, polyol or polyepoxide, denote substances which formally contain per molecule two or more of the functional groups that occur in their name.

A "primary amino group" is an $NH_2$ group which is bonded to an organic radical, and a "secondary amino group" is an NH group which is bonded to two organic radicals, which may also together be part of a ring.

The "amine hydrogen" refers to the hydrogen atoms of primary and secondary amino groups.

"Amine hydrogen equivalent weight" is the weight fraction of a hardener or of an amine per amine hydrogen present in the hardener or amine.

A "diluent" is a substance which is soluble in an epoxy resin and lowers its viscosity and which is not incorporated covalently into the resin matrix when the epoxy resin is cured.

The term "viscosity" in the present document refers to the dynamic viscosity or shear viscosity, which is defined by the ratio between the shearing stress and the shear rate (rate gradient) and is determined as described in the working examples.

A dashed line in the formulae in this document represents in each case the bond between a substituent and the remainder of the associated molecule.

"Molecular weight" is understood in the present document to be the molar mass (in grams per mole) of a molecule. "Average molecular weight" is the numerical average $M_n$ of an oligomeric or polymeric mixture of molecules, and is determined customarily by means of gel permeation chromatography (GPC) against polystyrene as standard.

"Room temperature" refers to a temperature of 23° C.

Preferably m is 0 or 1 or 2, more preferably 0 or 1, more particularly 0. These amines enable particularly low-viscosity epoxy resin compositions.

The amine of the formula (I) is preferably in the form of a technical mixture consisting primarily of amines of the formula (I) for which m is 0 or 1.

Preferably m is on average a value of less than 0.2.

More preferably m is on average a value in the range from 0 to 0.18, more particularly 0 to 0.15.

The hardener is preferably a nonaqueous hardener. A "nonaqueous hardener" in this context is a hardener which contains less than 5 weight %, preferably less than 2 weight %, more particularly less than 1 weight % of water.

Preferably X is 1,2-propylene. The methyl group thereof may be either in 1-position or in 2-position to the adjacent primary amino group. An amine of the formula (I) of this kind enables epoxy resin products having particularly low viscosity and particularly attractive surfaces.

Preferably Y is an aromatic hydrocarbon radical having 6 to 25, more particularly having 6 to 18, carbon atoms.

With particular preference Y is an aromatic hydrocarbon radical selected from the group consisting of

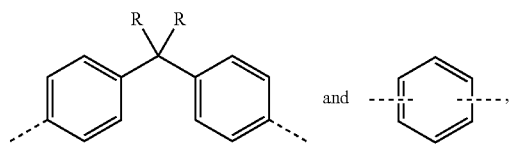

where R is a hydrogen radical or methyl radical.

An amine of the formula (I) of this kind is of particularly low viscosity, particularly ready accessibility, and particularly favorable cost.

If Y is the radical

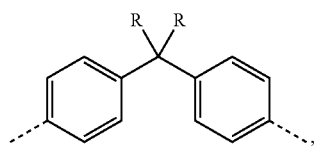

the amine of the formula (I) is derived more particularly from a liquid bisphenol A resin or from a liquid bisphenol F resin, or from a mixture of liquid bisphenol A and liquid bisphenol F resins, of the kind available commercially.

The amine of the formula (I) is preferably selected from the group consisting of

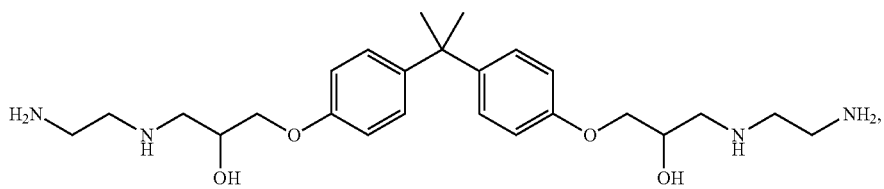

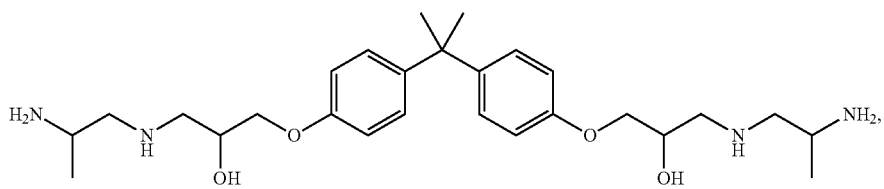

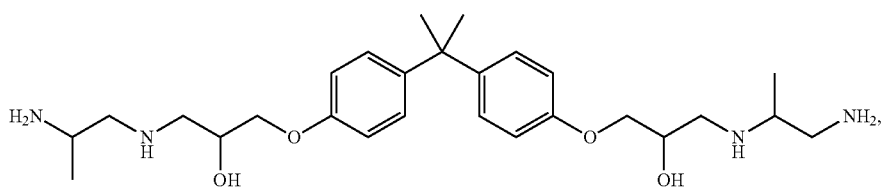

-continued
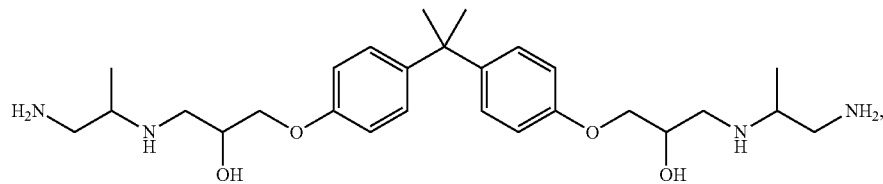
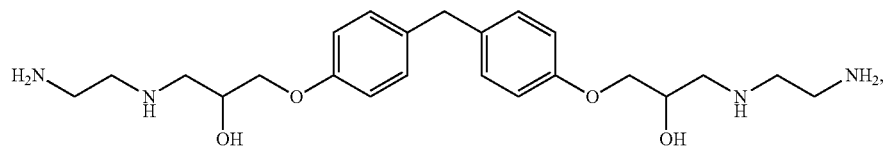
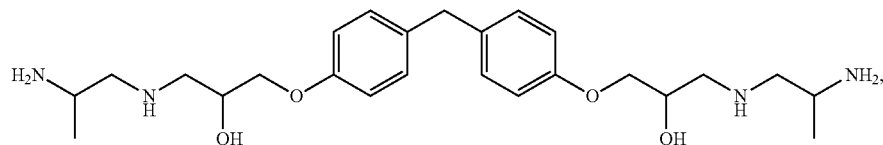
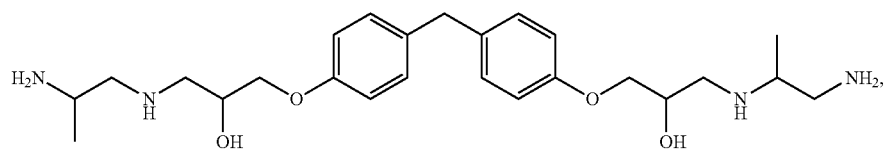
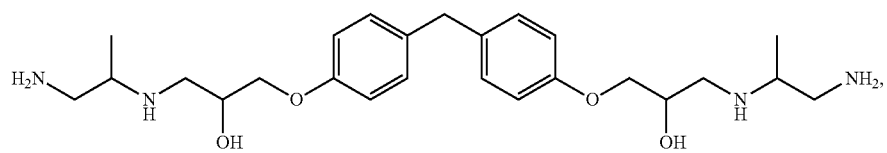
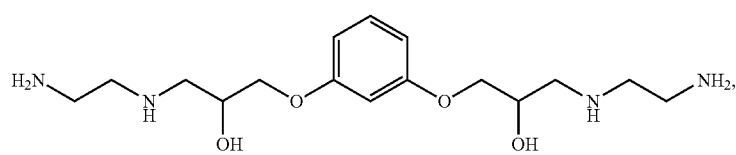
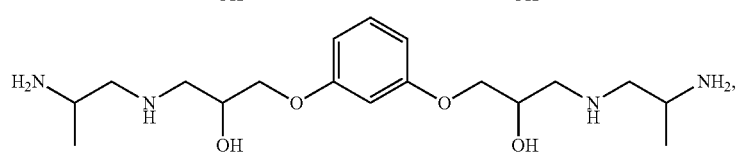
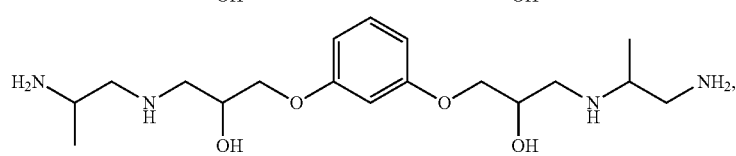
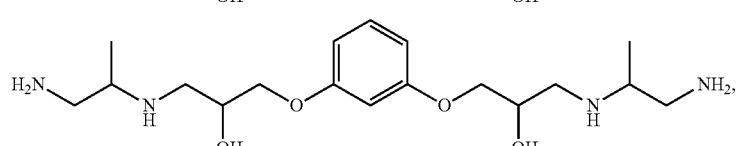
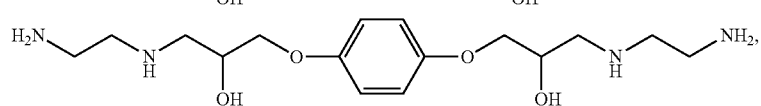
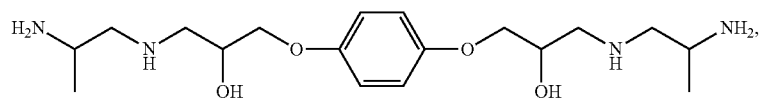
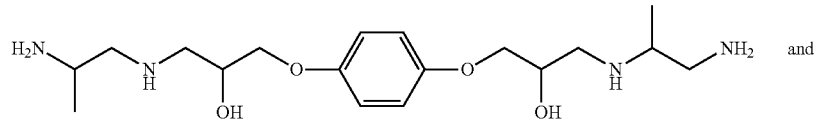 and

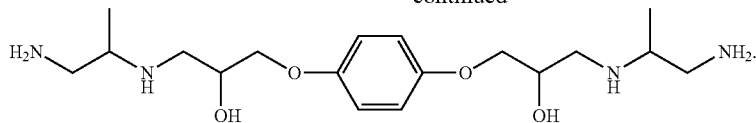

These amines of the formula (I) are particularly low in viscosity, particularly easy to access, particularly favorable in cost, and particularly compatible in customary epoxy resin compositions.

Particular preference is given to an amine of the formula (I) for which m is 0 to 1, X is 1,2-propylene, and Y is a radical of the formula

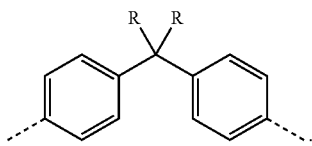

Preferably m is on average a value of less than 0.2.

More preferably m is on average a value in the range from 0 to 0.18, more particularly from 0 to 0.15.

An amine of this kind is particularly easy to access and has a particularly low tendency toward blushing effects.

An amine of the formula (I) is preferably obtained from the reaction of at least one diamine selected from 1,2-ethylenediamine and 1,2-propylenediamine with at least one diglycidyl ether of the formula (II).

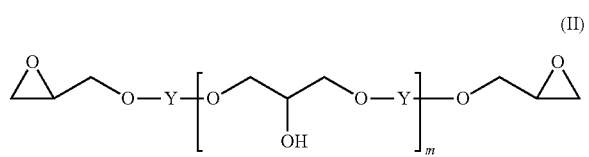

In the formula (II), m and Y have the definitions already stated.

The amine of the formula (I) for the described use is used preferably in the form of a reaction product from the reaction of at least one diamine selected from 1,2-ethylenediamine and 1,2-propylenediamine with at least one diglycidyl ether of the formula (II).

A preferred diamine for the reaction described is 1,2-propylenediamine. Such a reaction product has particularly low viscosity and enables epoxy resin products having particularly attractive surfaces.

Suitable diglycidyl ethers of the formula (II) are monocyclic or polycyclic aromatic diglycidyl ethers, especially technical epoxy resins, such as in particular the glycidylization products of:

bisphenol A, bisphenol F or bisphenol A/F, where A is acetone and F is formaldehyde, which have served as reactants in the preparation of these bisphenols. In the case of bisphenol F there may also be positional isomers present, derived more particularly from 2,4'- or 2,2'-hydroxyphenylmethane.

dihydroxybenzene derivatives such as resorcinol, hydroquinone or pyrocatechol;

further bisphenols such as bis(4-hydroxy-3-methylphenyl)methane, 2,2-bis(4-hydroxy-3-methylphenyl)propane (bisphenol C), bis(3,5-dimethyl-4-hydroxyphenyl)methane, 2,2-bis(3,5-dimethyl-4-hydroxyphenyl)propane, 2,2-Bis(4-hydroxy-3-tert-butylphenyl)propane, 2,2-bis(4-hydroxyphenyl)-butane (bisphenol B), 3,3-bis(4-hydroxyphenyl)pentane, 3,4-bis(4-hydroxy-phenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), bis(2-hydroxynaphth-1-yl)methane, bis(4-hydroxynaphth-1-yl)methane or 1,5-dihydroxynaphthalene.

Preferred as diglycidyl ethers of the formula (II) are bisphenol A diglycidyl ether, bisphenol F diglycidyl ether, bisphenol A/F diglycidyl ether, resorcinol diglycidyl ether or hydroquinone diglycidyl ether, especially technical grades available commercially.

Particularly preferred are bisphenol A diglycidyl ether, bisphenol F diglycidyl ether or bisphenol A/F diglycidyl ether, more particularly Araldite® GY 240, Araldite® GY 250, Araldite® GY 281, Araldite® GY 282, Araldite® GY 285, Araldite® PY 304 or Araldite® PY 720 (all from Huntsman), or D.E.R.® 330, D.E.R.® 331, D.E.R.® 332, D.E.R.® 336, D.E.R.® 351, D.E.R.® 352, D.E.R.® 354 or D.E.R.® 356 (all from Dow).

In the reaction, the ratio between the number of primary amino groups and the number of epoxide groups is preferably in the range from 2.5:1 to 25:1, more particularly 4:1 to 15:1.

The temperature during the reaction is preferably in the range from 40 to 120° C., more particularly 60 to 100° C.

Excess unreacted diamine is removed after the reaction, preferably by distillation, more particularly by thin-film or short-path distillation under reduced pressure.

The reaction product from this preparation may, in addition to the amine of the formula (I), have fractions of secondary products of relatively high molecular mass, more particularly in the form of multiply adducted diamine, as shown by way of example in the following formula for the case where m=0.

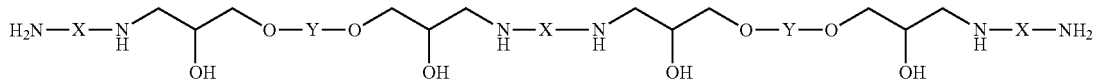

An amine of the formula (I) prepared in the manner described has a particularly low level of secondary products of relatively high molecular mass and is notable for particularly low viscosity and therefore particularly good properties in the use in accordance with the invention.

The amine of the formula (I) is therefore preferably used in the form of a reaction product from the reaction of at least one diamine selected from 1,2-ethylendiamine and 1,2-propylenediamine with at least one diglycidyl ether of the formula (II) where the ratio between the number of primary amino groups and the number of epoxide groups is at least 2.5:1 and excess diamine is removed by distillation after the reaction. The ratio between the number of primary amino groups and the number of epoxide groups is preferably in the range from 2.5:1 to 25:1, more particularly 4:1 to 15:1.

Surprisingly, a reaction product from this preparation has such a low viscosity that it is readily manageable at room temperature even without dilution.

The reaction product is preferably largely free from 1,2-ethylenediamine and/or 1,2-propylenediamine. More particularly it contains less than 1 weight %, preferably less than 0.5 weight %, more preferably less than 0.1 weight % of 1,2-ethylenediamine and/or 1,2-propylenediamine.

The amine of the formula (I) is used in a hardener for epoxy resins. The hardener per se is storage-stable, meaning that at room temperature in a suitable container, it can be kept for a relatively long time, typically for 3 to 6 months or longer, without suffering any alteration to a relevant extent in its application and service properties as a result of the storage, and therefore without losing its usefulness as a hardener for epoxy resins.

In a hardener for epoxy resins, the amine of the formula (I) is used preferably in combination with other amines and/or accelerators.

A further subject of the invention, accordingly, is a hardener, in particular a nonaqueous hardener, for epoxy resins comprising at least one amine of the formula (I) and at least one further amine and/or at least one accelerator. The further amine in this case is in particular not 1,2-ethylenediamine, not 1,2-propylenediamine, not an amine of the formula (I), not an amine of the formula (I) with values of m>3 and/or not a relatively high molecular mass secondary product in the form of multiply adducted diamine.

A hardener of this kind has particularly low viscosity and/or particularly high reactivity toward epoxy resins.

Suitable accelerators are substances which accelerate the reaction between amino groups and epoxide groups, more particularly acids or compounds which can be hydrolyzed to acids, more particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic esters, other organic or inorganic acids such as, in particular, phosphoric acid, or mixtures of the aforementioned acids and acid esters; tertiary amines such as, in particular, 1,4-diazabicyclo-[2.2.2]octane, benzyldimethylamine, α-methylbenzyldimethylamine, triethanol-amine, dimethylaminopropylamine, imidazoles such as, in particular, N-methyl-imidazole, N-vinylimidazole or 1,2-dimethylimidazole, salts of such tertiary amines, quaternary ammonium salts, such as, in particular benzyltrimethylammonium chloride, amidines such as, in particular, 1,8-diazabicyclo[5.4.0]-undec-7-ene, guanidines such as, in particular, 1,1,3,3-tetramethylguanidine, phenols, especially bisphenols, phenolic resins or Mannich bases such as, in particular, 2-(dimethylaminomethyl)phenol, 2,4,6-tris(dimethylaminomethyl)-phenol or polymers of phenol, formaldehyde and N,N-dimethyl-1,3-propane-diamine, phosphites such as, in particular, diphenyl or triphenyl phosphites, or compounds containing mercapto groups. Preferred accelerators are acids, tertiary amines or Mannich bases.

Most preferred is salicylic acid or 2,4,6-tris(dimethylaminomethyl)phenol or a combination thereof.

Especially suitable as further amine are polyamines which have at least two, more particularly at least three, amine hydrogens reactive toward epoxide groups, more particularly the following polyamines:

polyamines having one or two secondary amino groups, especially products from the reductive alkylation of primary aliphatic polyamines with aldehydes or ketones, especially N-benzyl-1,2-propanediamine, N,N'-dibenzyl-1,2-propanediamine, N-benzyl-1,3-bis(aminomethyl)benzene, N,N'-dibenzyl-1,3-bis(aminomethyl)benzene, N-2-ethylhexyl-1,3-bis(aminomethyl)benzene, N,N'-bis(2-ethylhexyl)-1,3-bis(aminomethyl)benzene, or partially styrenized polyamines such as, for example, styrenized MXDA (available as Gaskamine® 240 from Mitsubishi Gas Chemical);

aliphatic, cycloaliphatic or arylaliphatic primary diamines, especially 2,2-dimethyl-1,3-propanediamine, 1,3-pentanediamine (DAMP), 1,5-pentane-diamine, 1,5-diamino-2-methylpentane (MPMD), 2-butyl-2-ethyl-1,5-pentane-diamine (C11-neodiamine), 1,6-hexanediamine, 2,5-dimethyl-1,6-hexne-diamine, 2,2(4),4-trimethylhexamethylenediamine (TMD), 1,7-heptane-diamine, 1,8-octanediamine, 1,9-nonanediamine, 1,10-decanediamine, 1,11-undecanediamine, 1,12-dodecanediamine, 1,2-, 1,3- or 1,4-diamino-cyclohexane, bis(4-aminocyclohexyl)methane ($H_{12}$-MDA), bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methyl-cyclohexyl)methane, 1-amino-3-aminomethyl-3,5,5-trimethylcyclohexane (isophoronediamine or IPDA), 2- or 4-methyl-1,3-diaminocyclohexane or mixtures thereof, 1,3-bis(aminomethyl)cyclohexane, 1,4-bis(amino-methyl)cyclohexane, 2,5(2,6)-bis(aminomethyl)bicyclo[2.2.1]heptane (NBDA), 3(4),8(9)-bis(aminomethyl)tricyclo[$5.2.1.0^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(aminomethyl)-benzene (MXDA) or 1,4-bis(aminomethyl)benzene;

aliphatic primary di- or triamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl)polytetrahydrofurans or other polytetrahydrofurandiamines, cycloaliphatic ether group-containing diamines from the propoxylation and subsequent amination of 1,4-dimethylolcyclohexane, obtainable in particular as Jeffamine® RFD-270 (from Hunts-man), or polyoxyalkylenedi- or -triamines, which typically represent products from the amination of polyoxyalkylenedi- or -triols and are obtainable, for example, under the name Jeffamine® (from Huntsman), under the name Polyetheramine (from BASF) or under the name PC Amine® (from Nitroil). Especially suitable polyoxyalkylenedi- or -triamines are Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000, or corresponding amines from BASF or Nitroil;

polyamines containing secondary amino groups having two primary aliphatic amino groups, such as, in particular, 3-(2-aminoethyl)aminopropylamine, bis(hexamethylene)triamine (BHMT), diethylenetriamine (DETA), triethylenetetramine (TETA), tetraethylenepentamine (TEPA), pentaethylenehexamine (PEHA) or higher homologs of linear polyethyleneamines such as polyethylenepolyamine having 5 to 7 ethyleneamine units (referred to as "higher ethylenepolyamine", HEPA), products from the multiple cyanoethylation or cyanobutylation and subsequent hydrogenation of primary di- and polyamines having at least two primary amino groups, such as dipropylenetriamine (DPTA), N-(2-aminoethyl)-1,3-propanediam ine (N3-amine), N, N'-bis(3-aminopropyl)-ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N, N'-bis(3-amino-1-ethylpropyl)-2-methyl-1,5-pentanediam ine;

aliphatic, cycloaliphatic or arylaliphatic primary triamines, especially 4-aminomethyl-1,8-octanediamine, 1,3,5-tris(aminomethyl)benzene, 1,3,5-tris(aminomethyl)cyclohexane, tris(2-aminoethyl)amine, tris(2-amino-propyl)amine or tris(3-aminopropyl)amine;

aromatic polyamines, such as, in particular, m- and p-phenylenediamine, 4,4'-, 2,4' and/or 2,2'-diaminodiphenylmethane, 3,3'-dichloro-4,4'-diamino-diphenylmethane (MOCA), 2,4- and/or 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA), 3,3',5,5'-tetraethyl-4,4'-diaminodiphenylmethane (M-DEA), 3,3',5,5'-tetra-ethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraiso-propyl-4,4'-diaminodiphenylmethane (M-DIPA), 4,4'-diaminodiphenyl sulfone (DDS), 4-amino-N-(4-aminophenyl)benzenesulfonamide, 5,5'-methylene-dianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl (4-chloro-3,5-diaminobenzoate);

polyamidoamines, especially reaction products of a mono- or polybasic carboxylic acid, and/or the esters or anhydrides thereof, particularly of a dimer fatty acid, with an aliphatic, cycloaliphatic or aromatic polyamine that is used in a stoichiometric excess, more particularly a polyalkyleneamine such as, for example, DETA or TETA, more particularly the commercially available polyamidoamines Versamid® 100, 125, 140 or 150 (from Cognis), Aradur® 223, 250 or 848 (from Huntsman), Euretek® 3607 or 530 (from Huntsman) or Beckopox® EH 651, EH 654, EH 655, EH 661 or EH 663 (from Cytec);

phenalkamines, also called Mannich bases, especially reaction products of a Mannich reaction of phenols, more particularly cardanol, with aldehydes, more particularly formaldehyde, especially the commercially available phenalkamines Cardolite® NC-541, NC-557, NC-558, NC-566, Lite 2001, Lite 2002, NX-4943, NX-5607 or NX-5608 (from Cardolite), Aradur® 3440, 3441, 3442 or 3460 (from Huntsman) or Beckopox® EH 614, EH 621, EH 624, EH 628 or EH 629 (from Cytec);

adducts of 1,2-ethylenediamine or 1,2-propylenediamine with reactive diluents containing epoxide groups, more particularly monoglycidyl ethers of phenols, monoglycidyl or diglycidyl ethers of aliphatic or cycloaliphatic alcohols, diols or glycols, especially phenyl glycidyl ether, cresyl glycidyl ether, guaiacol glycidyl ether, 4-methoxyphenyl glycidyl ether, 4-n-butyl-phenyl glycidyl ether, 4-tert-butylphenyl glycidyl ether, 4-nonylphenyl glycidyl ether, 4-dodecylphenyl glycidyl ether, cardanol glycidyl ether, benzyl glycidyl ether, allyl glycidyl ether, butyl glycidyl ether, hexyl glycidyl ether, 2-ethyl-hexyl glycidyl ether, fatty alcohol glycidyl ethers such as, in particular $C_8$ to $C_{10}$ alkyl glycidyl ethers or $C_{12}$ to $C_{14}$ alkyl glycidyl ethers, 1,4-butanediol diglycidyl ether, 1,6-hexanediol diglycidyl ether, 1,4-cyclohexanedimethanol diglycidyl ether, or diglycidyl ethers of polyethylene glycols or polypropylene glycols;

and also secondary products of relatively high molecular mass from the above-described preparation of the amine of the formula (I), in particular in the form of multiply adducted diamines, as described above.

Preferred as further amine are polyamines having one or two secondary amino groups, especially N-benzyl-1,2-propanediamine, N-benzyl-1,3-bis(amino-methyl)benzene, N-2-ethylhexyl-1,3-bis(aminomethyl)benzene, or styrenized MXDA. Amines of this kind produce particularly low-viscosity hardeners, enabling epoxy resin compositions featuring particularly rapid curing and attractive surface.

Preferred as further amine are also primary diamines, more particularly MPMD, TMD, $H_{12}$-MDA, IPDA, 2- or 4-methyl-1,3-diaminocyclohexane, or mixtures thereof, 1,3-bis(aminomethyl)cyclohexane, 1,4-bis(aminomethyl)cyclohexane, NBDA or MXDA. Amines of this kind produce hardeners of particularly low viscosity.

Preferred as further amine, moreover, are ether group-containing aliphatic primary di- or triamines, more particularly polyoxyalkylene di- or -triamines having an average molecular weight in the range from 200 to 500 g/mol, especially Jeffamine® D-230 or Jeffamine® T-403 (both from Huntsman), or cycloaliphatic ether group-containing diamines from the propoxylation and subsequent amination of 1,4-dimethylolcyclohexane, especially Jeffamine® RFD-270 (from Huntsman). Amines of this kind produce particularly low-viscosity hardeners.

Additionally preferred as further amine are adducts of 1,2-ethylenediamine or 1,2-propylenediamine with reactive diluents containing epoxide groups, more particularly with cresyl glycidyl ether or $C_{12}$ to $C_{14}$ alkyl glycidyl ether or 1,4-butanediol diglycidyl ether or 1,6-hexanediol diglycidyl ether.

Especially preferred as further amine is N-benzyl-1,2-propanediamine. This amine produces hardeners of especially low viscosity which enable epoxy resin products which feature particularly good processing qualities, with rapid curing and attractive surface.

The hardener of the invention comprises preferably 1 to 80 weight %, preferably 2 to 70 weight %, more preferably 5 to 60 weight %, especially 10 to 50 weight %, of amine of the formula (I). Hardeners of this kind are notable for low viscosity and allow access to epoxy resin coatings having high cure rate, high hardness and attractive surfaces.

One particularly preferred hardener for epoxy resins comprises
  at least one amine of the formula (I),
  N-benzyl-1,2-propanediamine, and
  optionally at least one further amine and/or an accelerator.

In this case the amine of the formula (I), N-benzyl-1,2-propanediamine, and the further amine are present in an amount such that, of the overall amine hydrogens in the hardener,
  5 to 60% come from the amine of the formula (I),
  20 to 80% come from N-benzyl-1,2-propanediamine, and
  0 to 40% come from at least one further amine.

A hardener of this kind exhibits low viscosity and cures particularly rapidly and extensively without blushing effects to give cured films of high gloss and high hardness.

The hardener is preferably largely free from amines having a molecular weight below 120 g/mol, more particularly below 150 g/mol. The hardener contains preferably less than 2 weight %, more particularly less than 1 weight %, of amines having a molecular weight below 120 g/mol, more particularly below 150 g/mol.

A hardener of this kind has particularly toxicological and odor advantages and enables access to low-emission coatings having particularly attractive surfaces.

The hardener may further comprise at least one diluent, more particularly xylene, 2-methoxyethanol, dimethoxyethanol, 2-ethoxyethanol, 2-propoxy-ethanol, 2-isopropoxyethanol, 2-butoxyethanol, 2-phenoxyethanol, 2-benzyl-oxy-ethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as, for example, Solvesso® grades (from Exxon), alkylphenols such as tert-butyl-phenol, nonylphenol, dodecylphenol and 8,11,14-pentadecatrienylphenol (Cardanol, from cashew shell oil, available for example as Cardolite NC-700 from Cardolite Corp., USA), styrenized phenol, bisphenols, aromatic hydrocarbon resins, especially those containing phenol groups, alkoxylated phenol, especially ethoxylated or propoxylated phenol, more particularly 2-phenoxyethanol, adipates, sebacates, phthalates, benzoates, organic phosphoric acid esters or sulfonic acid esters or sulfonamides. Preferred are benzyl alcohol, dodecylphenol, tert-butylphenol, styrenized phenol, ethoxylated phenol, or aromatic hydrocarbon resins containing phenol groups, more particularly the Novares® grades LS 500, LX 200, LA 300 or LA 700 (from Rütgers).

The hardener preferably contains none or only a low level of diluents. With preference the hardener contains not more than 5 weight % of diluents.

The hardener may comprise further substances that are reactive toward epoxide groups, examples being monoamines such as hexylamine or benzylamine, or compounds containing mercapto groups, more particularly the following:
  liquid, mercaptan-terminated polysulfide polymers, known under the brand name Thiokol® (from Morton Thiokol; available for example from SPI Supplies, or from Toray Fine Chemicals), more particularly types LP-3, LP-33, LP-980, LP-23, LP-55, LP-56, LP-12, LP-31, LP-32 or LP-2; and also, moreover, under the brand name Thioplast® (from Akzo Nobel), more particularly the types G 10, G 112, G 131, G 1, G 12, G 21, G 22, G 44 or G 4;
  mercaptan-terminated polyoxyalkylene ethers, available for example by reaction of polyoxyalkylenediols or -triols either with epichlorohydrin or with an alkylene oxide, followed by sodium hydrogensulfide;
  mercaptan-terminated compounds in the form of polyoxyalkylene derivatives known under the brand name Capcure® (from Cognis), especially types WR-8, LOF or 3-800;
  polyesters of thiocarboxylic acids, for example pentaerythritol tetramercap-toacetate, trimethylolpropane trim ercaptoacetate, glycol dim ercaptoacetate, pentaerythritol tetra(3-mercaptopropionate), trimethylolpropane tri(3-mercaptopropionate) or glycol di-(3-mercaptopropionate), or products of esterification of polyoxyalkylenediols or -triols, of ethoxylated trimethylol-propane or of polyester diols with thiocarboxylic acids such as thioglycolic acid or 2- or 3-mercaptopropionic acid; or
  further compounds containing mercapto groups, such as, in particular, 2,4,6-trimercapto-1,3,5-triazine, 2,2'-(ethylenedioxy)diethanethiol (triethylene glycol dimercaptan) or ethanedithiol.

A further subject of the invention is an epoxy resin composition comprising
  a resin component comprising at least one epoxy resin and
  a hardener component comprising at least one amine of the formula (I) as described above.

In this case the resin component and the hardener component are typically present in containers separate from one another, and are not mixed with one another until immediately prior to application, so that their reactive groups come into contact with one another and the composition cures.

The hardener component is preferably nonaqueous and preferably contains less than 5 weight %, more preferably less than 2 weight %, more particularly less than 1 weight % of water.

The hardener component preferably comprises a hardener comprising at least one amine of the formula (I) and at least one further amine and/or at least one accelerator, as described above.

Suitability as epoxy resin is possessed by customary technical epoxy resins.

These are obtained in a known manner, as for example from the oxidation of the corresponding olefins or from the reaction of epichlorohydrin with the corresponding polyols, polyphenols or amines.

Particularly suitable as epoxy resin are what are called liquid polyepoxy resins, referred to hereinafter as "liquid resin". These have a glass transition temperature below 25° C.

Likewise possible as epoxy resin are what are called solid resins, which have a glass transition temperature above 25° C. and can be comminuted to powders which are pourable at 25° C.

Suitable epoxy resins are, in particular, aromatic epoxy resins, more particularly the glycidylization products of:
  bisphenol A, bisphenol F or bisphenol A/F, where A stands for acetone and F for formaldehyde, which served as reactants in the preparation of these bisphenols. In the case of bisphenol F, there may also be positional isomers present, derived more particularly from 2,4'- or 2,2'-hydroxyphenylmethane.

dihydroxybenzene derivatives such as resorcinol, hydroquinone or pyrochatechol;

further bisphenols or polyphenols such as bis(4-hydroxy-3-methylphe-nyl)methane, 2,2-bis(4-hydroxy-3-methylphenyl)propane (bisphenol C), bis-(3,5-dimethyl-4-hydroxyphenyl)methane, 2,2-bis(3,5-dimethyl-4-hydroxyphe-nyl)propane, 2,2-bis(3,5-dibromo-4-hydroxyphenyl)propane, 2,2-bis(4-hydro-xy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxy-phenyl)cyclohexane (bisphenol Z), 1,1-bis(4-hydroxyphenyl)-3,3,5-trimethyl-cyclohexane (bisphenol-TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), 4,4'-dihydroxybenzophenone, bis(2-hydroxynaphth-1-yl)methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;

condensation products of phenols with formaldehyde which are obtained under acidic conditions, such as phenol novolaks or cresol novolaks, also called bisphenol F novolaks;

aromatic amines, such as aniline, toluidine, 4-aminophenol, 4,4'-methylene-diphenyldiamine, 4,4'-methylenediphenyldi-(N-methyl)amine, 4,4-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, more particularly glycidyl ethers of saturated or unsaturated, branched or unbranched, cyclic or open-chain di-, tri- or tetrafunctional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneopentyl glycol, castor oil, trimethylolpropane, trimethylolethane, pentaerythritol, sorbitol or glycerol, or alkoxylated glycerol or alkoxylated trimethylolpropane;

a hydrogenated bisphenol A, F or A/F liquid resin, or the glycidylation products of hydrogenated bisphenol A, F or A/F;

a N-glycidyl derivative of amides or heterocyclic nitrogen bases, such as triglycidyl cyanurate or triglycidyl isocyanurate, or reaction products of epichlorohydrin with hydantoin.

epoxy resins from the oxidation of olefins, such as, in particular, vinylcyclo-hexene, dicyclopentadiene, cyclohexadiene, cyclododecadiene, cyclododecatriene isoprene, 1,5-hexadiene, butadiene, polybutadiene or divinylbenzene.

A preferred epoxy resin in the resin component is a liquid resin based on a bisphenol, more particularly a diglycidyl ether of bisphenol A, bisphenol F or bisphenol A/F, of the kind available commercially, for example, from Dow, Huntsman or Momentive. These liquid resins have a low viscosity for epoxy resins and in the cured state exhibit good properties as a coating. They may include fractions of solid bisphenol A resin or bisphenol F novolaks.

The resin component may comprise are active diluent, more particularly a reactive diluent having at least one epoxide group. Particularly suitable as reactive diluents are the glycidyl ethers of mono- or polyhydric phenols or aliphatic or cycloaliphatic alcohols, such as, in particular, the aforementioned polyglycidyl ethers of di- or polyols, or, furthermore, phenyl glycidyl ether, cresyl glycidyl ether, benzyl glycidyl ether, p-n-butylphenyl glycidyl ether, p-tert-butylphenyl glycidyl ether, nonylphenyl glycidyl ether, allyl glycidyl ether, butyl glycidyl ether, hexyl glycidyl ether, 2-ethylhexyl glycidyl ether, or glycidyl ethers of natural alcohols such as, in particular, $C_8$ to $C_{10}$ alkyl glycidyl ether or $C_{12}$ to $C_{14}$ alkyl glycidyl ether. The addition of a reactive diluent to the epoxy resin has the effect of reducing the viscosity, and/or of reducing the glass transition temperature and/or the mechanical values.

The epoxy resin composition optionally comprises further constituents, particularly auxiliaries and adjuvants customarily used in epoxy resin compositions, examples being the following:

solvents, diluents, film-forming assistants or extenders, such as especially the aforementioned diluents;

reactive diluents, especially reactive diluents containing epoxide groups, as mentioned above, epoxidized soybean oil or linseed oil, compounds containing acetoacetate groups, especially acetoacetylated polyols, butyrolactone, carbonates, aldehydes, and also, moreover, isocyanates or silicones containing reactive groups;

polymers, especially polyam ides, polysulfides, polyvinylformal (PVF), polyvinylbutyral (PVB), polyurethanes (PU), polymers with carboxyl groups, polyamides, butadiene-acrylonitrile copolymers, styrene-acrylonitrile copolymers, butadiene-styrene copolymers, homo- or copolymers of unsaturated monomers, especially from the group encompassing ethylene, propylene, butylene, isobutylene, isoprene, vinyl acetate or alkyl (meth)acrylates, especially chlorosulfonated polyethylenes or fluorine-containing polymers, sulfonamide-modified melamines or purified Montan waxes;

inorganic or organic fillers, especially ground or precipitated calcium carbonates, with or without a coating of fatty acids, more particularly of stearates, barytes (heavy spar), talcs, finely ground quartzes, silica sand, iron mica, dolomites, wollastonites, kaolins, mica (potassium aluminum silicate), molecular sieves, aluminum oxides, aluminum hydroxides, magnesium hydroxide, silicas, cements, gypsums, flyashes, carbon black, graphite, metal powders such as aluminum, copper, iron, zinc, silver or steel, PVC powders or hollow beads;

fibers, especially glass fibers, carbon fibers, metal fibers, ceramic fibers, or polymeric fibers such as polyamide fibers or polyethylene fibers;

pigments, especially titanium dioxide and/or iron oxides;

the aforementioned accelerators;

rheology modifiers, especially thickeners or antisettling agents;

adhesion promoters, especially organoalkoxysilanes;

stabilizers against oxidation, heat, light or UV radiation;

flame retardants, especially aluminum hydroxide (ATH), magnesium dihydroxide (MDH), antimony trioxide, antimony pentoxide, boric acid $(B(OH)_3)$, zinc borate, zinc phosphate, melamine borate, melamine cyanurate, ammonium polyphosphate, melamine phosphate, melamine pyrophosphate, polybrominated diphenyl oxides or diphenyl ethers, phosphates such as especially diphenyl cresyl phosphate, resorcinol bis(diphenyl phosphate), resorcinol diphosphate oligomer, tetraphenylresorcinol diphosphite, ethylenediamine diphosphate or bisphenol A bis(diphenyl phosphate), tris(chloroethyl) phosphate, tris(chloro-propyl) phosphate or tris(dichloroisopropyl) phosphate, tris[3-bromo-2,2-bis-(bromomethyl)propyl] phosphate, tetrabromobisphenol A, bis(2,3-dibromo-propyl ether) of bisphenol A, brominated epoxy resins, ethylenebis(tetrabro-mophthalimide), ethylenebis(dibromonorbornanedicarboximide), 1,2-bis-(tribromophenoxy)ethane, tris(2,3-dibromopropyl) isocyanurate, tribromophenol, hexabromocyclododecane, bis(hexachlorocyclopentadieno)cyclooctane or chlorinated paraffins;

surface-active substances, especially wetting agents, flow control agents, deaerating agents or defoamers;

biocides, such as, for example, algicides, fungicides or fungal growth inhibitors.

The epoxy resin composition preferably comprises further auxiliaries and adjuvants, especially wetting agents, flow control agents, defoamers, stabilizers, pigments and/or accelerators, especially salicylic acid and/or 2,4,6-tris(dimethylaminomethyl)phenol.

The epoxy resin composition preferably contains none or only a small amount of diluents, preferably not more than 5 weight %, especially not more than 2 weight %.

The ratio of the number of groups that are reactive toward epoxide groups in the epoxy resin composition, to the number of epoxide groups, is preferably in the range from 0.5 to 1.5, more particularly 0.7 to 1.2.

When mixing the resin component and the hardener component, the amine hydrogens and, where present, other groups that are reactive toward epoxide groups, present in the epoxy resin composition, react with the epoxide groups with ring-opening of the latter groups (addition reaction). As a result of these reactions, the composition undergoes polymerization and ultimately cures. The person skilled in the art is aware that primary amino groups are difunctional groups with respect to epoxide groups, and a primary amino group therefore counts as two groups that are reactive toward epoxide groups.

The two components of the epoxy resin composition are each stored in their own container. Further constituents of the epoxy resin composition may be present as part of the resin component or of the hardener component, with further constituents that are reactive toward epoxide groups preferably being part of the hardener component. A suitable container for storing the resin component or the hardener component is, in particular, a drum, a hobbock, a pouch, a pail, a canister, a cartridge or a tube. The components are storable, meaning that they can be kept for several months up to a year or more before being employed, without suffering alteration in their respective properties to any extent relevant for their use. For the use of the epoxy resin composition, the resin component and the hardener component are mixed with one another shortly before or during application. The mixing ratio between the two components is preferably selected such that the groups of the hardener component that are reactive toward epoxide groups are present in an appropriate ratio to the epoxide groups of the resin component, as described above. In terms of parts by weight, the mixing ratio between the resin component and the hardener component is customarily in the range from 1:10 to 10:1.

The two components are mixed by means of suitable method; this may take place continuously or batchwise. If mixing takes place prior to application, it should be ensured that not too much time elapses between the mixing of the components and application, since otherwise there may be disruptions, such as retarded or incomplete development of adhesion to the substrate, for example. Mixing takes place in particular at ambient temperature, which is typically in the range from about 5 to 50° C., preferably at about 10 to 30° C. The mixing of the two components is at the same time the start of curing through chemical reaction, as described above. Curing especially takes place at ambient temperature. It typically extends over several days to weeks, until it has largely been completed under the given conditions. The duration is dependent on factors including the temperature, the reactivity of the constituents and their stoichiometry, and also the presence of accelerators.

A further subject of the invention is thus also a cured composition obtained from the curing of an epoxy resin composition as described in the present document.

The epoxy resin composition is applied to at least one substrate, those below being particularly suitable:

glass, glass-ceramic, concrete, mortar, brick, tile, plaster or natural stones such as granite or marble;

metals or alloys such as aluminum, iron, steel or nonferrous metals, or surface-enhanced metals or alloys such as galvanized or chromed metals;

leather, textiles, paper, wood, woodbase materials bonded with resins, such as phenolic, melamine or epoxy resins, for example, resin-textile composites, or other polymer composites;

plastics, especially rigid or flexible PVC, ABS, polycarbonate (PC), polyamide (PA), polyesters, PMMA, epoxy resins, PU, POM, PO, PE, PP, EPM or EPDM, the plastics having optionally been surface-treated by plasma, corona or flame treatment;

fiber-reinforced plastics, such as carbon fiber-reinforced plastics (CRP), glass fiber-reinforced plastics (GRP) or sheet molding compounds (SMC);

coated substrates, such as powder-coated metals or alloys; paints or varnishes.

As and when necessary, the substrates may be pretreated before the epoxy resin composition is applied. Such pretreatments include, in particular, physical and/or chemical cleaning techniques, as for example sanding, sandblasting, shotblasting, brushing and/or blowing, and also, furthermore, treatment with cleaners or solvents, or the application of an adhesion promoter, an adhesion promoter solution or a primer.

The epoxy resin composition described can be used with advantage as a fiber composite matrix for fiber composite materials (composites) such as, in particular, CRP or GRP, or as an encapsulating compound, sealant, adhesive, covering, coating, paint, varnish, seal, priming coat or primer.

In particular it can be used as an encapsulating compound, for example as an electrical encapsulating compound, or as an adhesive, more particularly as a bodywork adhesive, sandwich element adhesive, half-shell adhesive for rotor blades of wind turbines, bridge element adhesive or anchoring adhesive.

In particular it can, furthermore, be used as a covering, coating paint, varnish, seal, priming coat or primer for construction and industry applications, more particularly as a floor covering or floor coating for interiors such as offices, industrial halls, sports halls or cooling rooms, or in the exterior segment, for balconies, terraces, parking decks, bridges or roofs, as a protective coating for concrete, cement, metals, plastics or wood, for the surface sealing of wooden constructions, vehicles, loading areas, tanks, silos, shafts, piping circuits, pipelines, machines or steel constructions, for example, such as of boats, piers, offshore platforms, sluice gates, hydroelectric power stations, river constructions, swimming pools, wind turbines, bridges, chimneys, cranes or sheet-pile walls, for example.

In particular it can, furthermore, be used as an undercoat, tie coat, anticorrosion primer, or for rendering surfaces hydrophobic.

The fully or partly cured epoxy resin composition, especially when used as a coating, covering or paint, may have a further coating, covering or paint applied to it, in which case this further layer may likewise comprise an epoxy resin composition, or else may comprise a different material, particularly a polyurethane coating or polyurea coating.

With particular advantage the epoxy resin composition described is used as a coating.

A further subject of the invention, accordingly, is a coating comprising an epoxy resin composition as described above.

The term "coating" refers to flatly applied coverings of all kinds, more particularly paint coats, varnish coats, seal coats, primer coats or primers, as described above, or floorcoverings or protective coatings, including in particular those for heavy-duty corrosion prevention.

With particular advantage, the epoxy resin composition described is used in low-emission products that carry eco-quality seals, according for example to Emicode (EC1 Plus), AgBB, DIBt, Der Blaue Engel, AFSSET, RTS (M1), and U.S. Green Building Council (LEED).

As a coating, the epoxy resin composition is used advantageously in a method for coating, where it has a liquid consistency with low viscosity and good leveling properties and is applied more particularly as a self-leveling or thixotrope coating to predominantly planar surfaces or as a paint. In the context of this application, the viscosity of the epoxy resin composition immediately after the mixing of the resin and hardener components, and as measured at 20° C., is preferably in the range from 300 to 4000 mPa·s, preferably in the range from 300 to 2000 mPa·s, more particularly in the range from 300 to 1500 mPa·s. Within the working time, the mixed composition is applied two-dimensionally as a thin film having a layer thickness of typically about 50 μm to about 5 mm to a substrate, typically at ambient temperature. Application is accomplished in particular by pouring the composition onto the substrate that is to be coated, and then spreading it evenly with the aid, for example, of a doctor blade or toothed applicator. Application may alternatively take place with a brush or roller or by spray application, as an anticorrosion coating on steel, for example.

Curing is typically accompanied by the development of largely clear, glossy and nonsticky films of high-hardness, which exhibit effective adhesion to a very wide variety of substrates.

The use of the epoxy resin composition results in an article comprising the cured composition from the curing of the epoxy resin composition described. The cured composition is present more particularly in the form of a coating.

The epoxy resin composition described is notable for advantageous properties. It is low in viscosity and in odor, and cures rapidly and extensively without blushing effects, even with small fractions or entirely without the use of diluents, and in particular even without the use of volatile amines of intense odor. When used two-dimensionally as a coating, it results in clear, nontacky films with high hardness and high surface quality which undergo hardly any yellowing under the influence of light. With the epoxy resin composition described it is possible in particular to obtain low-emission epoxy resin products which meet the conditions for numerous eco-quality seals and at the same time satisfy exacting demands in terms of workplace safety, processing properties, and service properties.

A further subject of the invention is an amine of the formula (I) for which
m is 0 to 1,
X is 1,2-propylene, and
Y is a radical of the formula

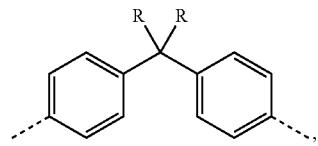

where R is a hydrogen radical or methyl radical.

Preferably m is on average a value of less than 0.2.

More preferably m is on average a value in the range from 0 to 0.18, more particularly 0 to 0.15.

This amine is especially suitable for use in a hardener for epoxy resins, as described above.

It has the advantageous properties already stated.

EXAMPLES

Set out below are working examples which are intended to elucidate in more detail the invention described. The invention is of course not confined to these working examples described.

"AHEW" stands for the amine hydrogen equivalent weight.

"EEW" stands for the epoxide equivalent weight.

"Standard conditions" refer to a temperature of 23±1° C. and a relative atmospheric humidity of 50±5%. "SC" stands for "standard conditions".

Description of Measurement Methods:

Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers (cm$^{-1}$); (measuring window: 4000-650 cm$^{-1}$).

The viscosity was measured on a thermostated cone/plate viscometer, Rheotec RC30 (cone diameter 50 mm, cone angle 1°, cone tip/plate distance 0.05 mm, shear rate 10 s$^{-1}$).

The amine number was determined by titration (with 0.1N HClO$_4$ in acetic acid against crystal violet).

Substances Used:

Araldite® GY 250: bisphenol A diglycidyl ether, EEW about 187.5 g/eq (from Huntsman)

Araldite® DY-E: monoglycidyl ether of C$_{12}$ to C$_{14}$ alcohols, EEW about 290 g/eq (from Huntsman)

Erisys® RDGE-H: resorcinol diglycidyl ether, EEW about 118.5 g/eq (from Emerald Performance Materials)

N-Benzyl-1,2-propanediamine: reaction mixture prepared as described below, AHEW about 54.75 g/eq N-Benzyl-1,2-propanediamine A round-bottomed flask was charged at room temperature with 444.8 g (6 mol) of 1,2-propanediamine under a nitrogen atmosphere. With thorough stirring, a solution of 212.2 g (2 mol) of benzaldehyde in 1500 ml of isopropanol was added slowly dropwise with stirring continued for 2 hours thereafter. The reaction mixture was subsequently hydrogenated under a hydrogen pressure of 90 bar at a temperature of 85° C. and with a flow rate of 5 ml/min on a continuous hydrogenation apparatus with Pd/C fixed-bed catalyst. For reaction monitoring, IR spectroscopy was used to verify whether the imine band at about 1665 cm$^{-1}$ had disappeared. At that point the hydrogenated solution was concentrated at 65° C. on a rotary evaporator, with removal of unreacted 1,2-propanediamine and isopropanol. This gave a clear, slightly yellowish liquid. Of this, 300 g were distilled under reduced pressure at 80° C., and 237.5 g of distillate with a vapor temperature of 60 to 63° C. at 0.08 to 0.09 bar were collected. This gave a colorless liquid having a viscosity of 8.5 mPa·s at 20° C. and an amine number of 682 mg KOH/g, which, according to $^1$H-NMR, represents a mixture of $N^1$-benzyl-1,2-propanediamine and $N^2$-benzyl-1,2-propanediamine in a ratio of about 2/1, which according to GC-FID had a purity of >97%.

Preparation of Amines of Formula (I):

Amine 1:

148.3 g (2 mol) of 1,2-propylenediamine were introduced under a nitrogen atmosphere and heated to 80° C. With thorough stirring, a solution of 37.4 g (0.1 mol) of Araldite® GY-250 in 500 ml of hot (50° C.) isopropanol was added slowly dropwise, with the temperature of the reaction mixture being maintained at between 70 and 85° C. by cooling. The reaction mixture was then left at 80° C. for 2 hours, after which the volatile constituents (isopropanol and excess 1,2-propanediamine) were removed by distillation. This gave a clear, slightly yellowish liquid of high viscosity, having a viscosity at 60° C. of 86.9 Pa·s and an amine number of 420.9 mg KOH/g.

FT-IR: 2960, 2923, 2868, 1606, 1581, 1508, 1455, 1295, 1245, 1181, 1034, 825.

Amine 2:

148.3 g (2 mol) of 1,2-propylenediamine were introduced under a nitrogen atmosphere and heated to 80° C. With thorough stirring, a solution of 23.7 g (0.1 mol) of Erisys® RDGE-H in 350 ml hot (50° C.) isopropanol was added slowly dropwise, with the temperature of the reaction mixture being maintained at between 70 and 85° C. by cooling. The reaction mixture was then left at 80° C. for 2 hours, after which the volatile constituents (isopropanol and excess 1,2-propanediamine) were removed by distillation. This gave a clear, slightly yellowish liquid having a viscosity at 60° C. of 13.2 Pa·s and an amine number of 553.5 mg KOH/g.

FT-IR: 2955, 2921, 2869, 1589, 1490, 1450, 1286, 1263, 1181, 1145, 1039, 831, 760, 686.

Amine 3:

120.2 g (2 mol) of 1,2-ethylenediamine were introduced under a nitrogen atmosphere and heated to 80° C. With thorough stirring, a solution of 37.4 g (0.1 mol) of Araldite® GY-250 in 500 ml hot (50° C.) isopropanol was added slowly dropwise, with the temperature of the reaction mixture being maintained at between 70 and 85° C. by cooling. The reaction mixture was then left at 80° C. for 2 hours, after which the volatile constituents (isopropanol and excess 1,2-propanediamine) were removed by distillation. This gave a clear, slightly yellowish liquid of high viscosity, having a viscosity at 60° C. of 60.0 Pa·s (shear rate 5 s$^{-1}$) and an amine number of 440.5 mg KOH/g.

Preparation of an Amine as Comparison:

Amine 4:

148.3 g (2 mol) of 1,3-propylenediamine were introduced under a nitrogen atmosphere and heated to 80° C. With thorough stirring, a solution of 37.4 g (0.1 mol) of Araldite® GY-250 in 500 ml hot (50° C.) isopropanol was added slowly dropwise, with the temperature of the reaction mixture being maintained at between 70 and 85° C. by cooling. The reaction mixture was then left at 80° C. for 2 hours, after which the volatile constituents (isopropanol and excess 1,3-propylenediamine) were removed by distillation. This gave a clear, slightly yellowish liquid of high viscosity, having a viscosity at 60° C. of 30.5 Pa·s (shear rate 5 s$^{-1}$) and an amine number of 417.6 mg KOH/g.

Production of Hardeners and Epoxy Resin Compositions

For each example, the ingredients of the hardener component specified in table 1 were mixed in the stated quantities (in parts by weight) using a centrifugal mixer (SpeedMixer™ DAC 150, FlackTek Inc.) and the mixtures were stored in the absence of moisture.

Similarly, the ingredients of the resin component as specified in table 1 were processed and stored.

Thereafter the two components of each composition were processed to a homogeneous liquid using the centrifugal mixer, and this liquid was tested immediately as follows:

10 minutes after mixing, the viscosity at 20° C. was ascertained ("viscosity (10')").

A first film was drawn down in a film thickness of 500 μm onto a glass plate, which was stored/cured under standard conditions. Determined on this film was the König hardness (pendulum hardness as König, measured to DIN EN ISO 1522) after 1 day ("König hardness (1 d SC)"), after 2 days ("König hardness (2 d SC)"), after 4 days ("König hardness (4 d SC)"), after 7 days ("König hardness (7 d SC)"), and after 14 days ("König hardness (14 d SC)"). After 14 days, the appearance of the film was assessed (identified in the table as "appearance (SC)". A film identified as "attractive" there was clear and had a glossy and nonsticky surface without structure. "Structure" here refers to any kind of marking or pattern on the surface.

A second film was drawn down onto a glass plate in a film thickness of 500 μm, and this film immediately after application was stored, or cured, at 8° C. and at 80% relative humidity for 7 days and subsequently under standard conditions (SC) for 3 weeks. 24 hours after application, a polypropylene bottle cap was placed onto the film, with a moist sponge placed beneath the cap. After a further 24 hours, the sponge and the cap were removed and were placed on a new site on the film, where, after 24 hours, they were removed again and placed anew, a total of 4 times. Thereafter the appearance of this film was assessed (identified in the tables as "appearance (8°/80%)"), in the same way as described for the appearance (SC). Also reported here in each case is the number of marks visible in the film as a result of the wet sponge and/or the applied cap. On the films cured in this way, the König hardness was again determined, in each case after 7 days at 8° C. and 80% relative humidity ("König hardness (7 d 8°/80%)"), then after a further 2 days under SC ("König hardness (+2 d Sc)"), 7 days under SC ("König hardness (+7 d SC)"), and after 14 days under SC ("König hardness (+14 d Sc)").

The results are reported in table 1.

TABLE 1

Composition and properties of Ex-1 to Ex-5 and Ref-1 and Ref-2.

|  | Ex-1 | Ex-2 | Ex-3 | Ex-4 | Ex-5 | Ref-1 | Ref-2 |
|---|---|---|---|---|---|---|---|
| Resin comp.: | | | | | | | |
| Araldite ® GY-250 | 167.2 | 167.2 | 167.2 | 167.2 | 167.2 | 167.2 | 167.2 |
| Araldite ® DY-E | 31.8 | 31.8 | 31.8 | 31.8 | 31.8 | 31.8 | 31.8 |
| Hardener comp.: | | | | | | | |
| Amine 1 | 51.3 | 30.8 | — | — | — | — | — |
| Amine 2 | — | — | 32.1 | — | — | — | — |
| Amine 3 | — | — | — | 49.7 | 39.8 | — | — |
| Amine 4 | — | — | — | — | — | 51.3 | 41.0 |
| N-Benzyl-1,2-propanediamine | 25.6 | 37.3 | 27.4 | 24.9 | 35.9 | 25.6 | 31.5 |
| Viscosity (10') [Pa · s] | 5.0 | 1.5 | 3.4 | 10.6 | 5.0 | 11.1 | 4.7 |
| König hardness [s] | | | | | | | |
| (1 d SC) | 81 | 77 | 95 | 83 | 89 | 83 | 129 |
| (2 d SC) | 126 | 132 | 127 | 84 | 132 | 105 | 163 |
| (4 d SC) | 155 | 165 | 132 | 120 | 173 | 147 | 191 |
| (7 d SC) | 172 | 166 | 157 | 147 | 194 | 183 | 204 |
| (14 d SC) | 179 | 181 | n.d. | 209 | 209 | 208 | 210 |
| Appearance (SC) | attractive | attractive | attractive | slight marking | slight marking | slight marking | slight marking |
| König hardness [s] | | | | | | | |
| (7 d 8°/80%) | 12 | 19 | 8 | 11 | 18 | 7 | 11 |
| (+2 d SC) | 13 | 36 | 13 | 13 | 28 | 21 | 11 |
| (+7 d SC) | 15 | 38 | n.d. | 20 | 60 | 27 | 38 |
| (+14 d SC) | 17 | 50 | n.d. | 25 | 143 | 50 | 73 |
| Appearance (8°/80%) | slightly dull | slightly dull | slightly matt | dull, uneven | dull, uneven | dull, uneven | dull, uneven |
| Number of marks | 4[1] | 2 | 2 | 1 | 1 | 1 | 1 |

"n.d." stands for "not determined"

[1] faint

The invention claimed is:

1. A method comprising hardening epoxy resins with an amine of formula (I),

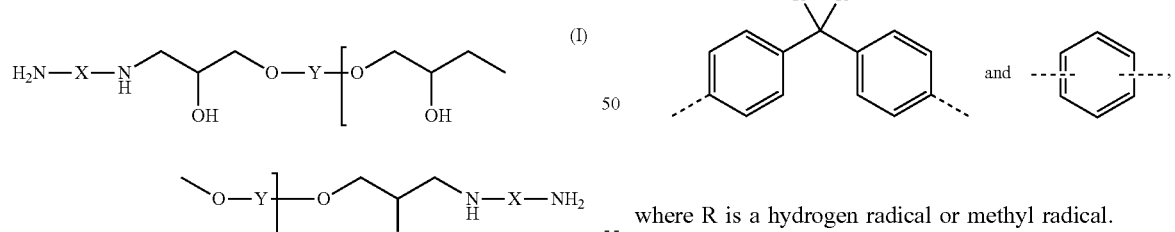

where:
  m is 0 to 3,
  X is 1,2-propylene, and
  Y is a monocyclic or polycyclic aromatic hydrocarbon radical.

2. The method as claimed in claim 1, wherein the hardener is a nonaqueous hardener.

3. The method as claimed in claim 1, wherein Y is an aromatic hydrocarbon radical selected from the group consisting of

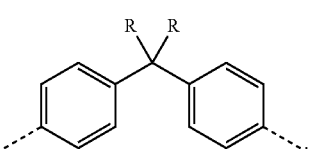

where R is a hydrogen radical or methyl radical.

4. The method as claimed in claim 1, wherein m is 0 to 1, Y is a radical of the formula where R is a hydrogen radical or methyl radical.

5. An amine of formula (I),

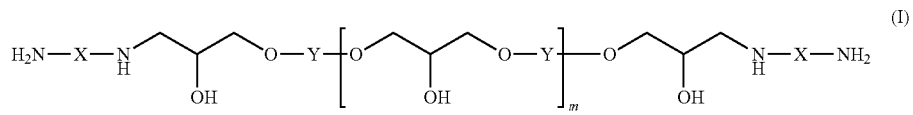

where:
   m is 0 to 1,
   X is 1,2-propylene,
   Y is a radical of formula

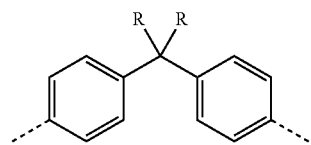

and
R is a hydrogen radical or methyl radical.

6. An amine of formula (I),

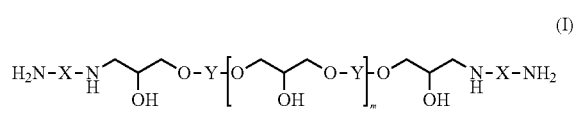

where:
   m is 0 to 3,
   X is 1,2-propylene, and
   Y is a monocyclic or polycyclic aromatic hydrocarbon radical.

7. A reaction product produced from a reaction of at least 1,2-propylenediamine with at least one diglycidyl ether of formula (II):

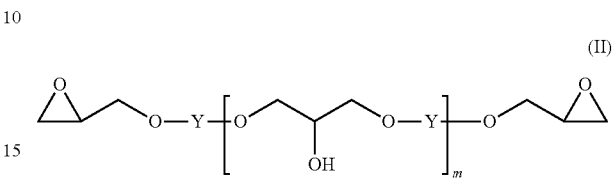

the reaction product comprising the amine of formula (I) as claimed in claim 6 in a hardener for epoxy resins.

8. The product as claimed in claim 7, wherein the ratio between the number of primary amino groups and the number of epoxide groups is at least 2.5:1 and excess diamine is removed by distillation after the reaction.

9. The product as claimed in claim 7, wherein the reaction product contains less than 1 weight % of 1,2-propylenediamine.

10. A hardener for epoxy resins, comprising the amine of formula (I) as claimed in claim 6 and at least one further amine and/or at least one accelerator.

11. The hardener as claimed in claim 10, wherein the further amine comprises N-benzyl-1,2-propanediamine.

12. The hardener as claimed in claim 10, wherein 1 to 80 weight % of the amine of formula (I) is present.

13. An epoxy resin composition comprising
    a resin component comprising at least one epoxy resin, and
    a hardener component comprising the amine of formula (I) as claimed in claim 6.

14. A coating comprising the epoxy resin composition as claimed in claim 13.

15. A cured composition obtained by curing the epoxy resin composition as claimed in claim 13.

* * * * *